United States Patent [19]

Wilson et al.

[11] Patent Number: 5,625,128
[45] Date of Patent: Apr. 29, 1997

[54] NON-HUMAN ANIMAL MODEL OF A HUMAN AIRWAY

[75] Inventors: James M. Wilson; John F. Engelhardt, both of Ann Arbor, Mich.

[73] Assignee: The Regents of the University of Michigan, Ann Arbor, Mich.

[21] Appl. No.: 445,072

[22] Filed: May 19, 1995

Related U.S. Application Data

[63] Continuation of Ser. No. 943,952, Sep. 11, 1992, abandoned.

[51] Int. Cl.$^6$ .................. C12N 5/00; C12N 15/00; A66K 51/00
[52] U.S. Cl. .................. 800/2; 800/DIG. 5; 424/9.1
[58] Field of Search .................. 800/2, DIG. 5; 424/9

[56] References Cited

FOREIGN PATENT DOCUMENTS

| | | | |
|---|---|---|---|
| 0469632A1 | 2/1992 | European Pat. Off. | C12Q 1/18 |
| WO9004017 | 4/1990 | WIPO | C12N 5/00 |
| WO9116451 | 10/1991 | WIPO | C12Q 1/04 |
| WO9116910 | 11/1991 | WIPO | A61K 35/00 |
| WO9118615 | 12/1991 | WIPO | A61K 35/00 |

OTHER PUBLICATIONS

J.R. Yankaskas et al., "Persistence of Abnormal Chloride Ion Permeability in Cystic Fibrosis Nasal Epethelial Cells in Heterologous Culture", *The Lancet*, pp. 954–956 (Apr. 1985).
M. Shiba et al., "An Open–Ended Rat Tracheal Implant Model: Toxic Effects of Formaldehyde on the Respiratory Epithelium", *Toxic. Lett.*, 16, pp. 241–248 (1983).
M. Shiba et al., "The Effects of Formaldehyde Gas in a Flow–Through Rat Tracheal Implant System", *Toxicology*, 30, pp. 317–925 (1984).
M.L. Drumm et al., "Correction of the Cystic Fibrosis Defect In Vitro by Retrovirus–Mediated Gene Transfer", *Cell*, 6, 1227–33, (1990).
M. Barinaga, "Knockout Mice Offer First Animal Model for CF", *Science*, 257, pp. 1046–1047 (1992).
L.L. Clarke et al., "Defective Epithelial Chloride Transport in a Gene–Targeted Mouse Model of Cystic Fibrosis", *Science*, 257, pp. 1125–1128 (1992).

F.S. Collins, "Cystic Fibrosis: Molecular Biology and Therapeutic Implications", *Science*, 256, pp. 774–779 (1992).
J.F. Engelhardt et al., "Reconstitution of tracheal grafts with a genetically modified epithelium", *Proc. Natl. Acad. Sci.*, 88, pp. 11192–11196 (1991).
Y. Inayama et al., "The Differentiation Potential of Tracheal Basal Cells", *Lab. Invest.*, 58, pp. 706–717 (1988).
Y. Inayama et al., "In Vitro and In Vivo Growth and Differentiation of Clones of Tracheal Basal Cells", *Am. J. Path.*, 134, pp. 539–549 (1989).
A.J.P. Klein–Szanto et al., "Propagation of Normal Human Epithelial Cell Populations Using an in Vivo Culture System", *Am. J. Path.*, 108, pp. 231–239 (1982).
T. Obara et al., "Rapid Detection of Xenotransplanted Human Tissues Using In Situ Hybridization", *Am. J. Path.*, 122, pp. 386–391 (1986).
T. Obara et al., "Localization of Keratin mRNA in Human Tracheobronchial Epithelium and Bronchogenic Carcinomas by In Situ Hybridization", *Am. J. Path.*, 131, pp. 519–529 (1988).
M. Terzaghi et al., "Repopulation of Denuded Tracheal Grafts with Normal, Preneoplastic, and Neoplastic Epithelial Cell Populations", *Cancer Res.*, 38, pp. 4546–4553 (1978).
H. Ura et al., "Effects of Formaldehyde on Normal Xenotransplanted Human Tracheobronchial Epithelium", *Am. J. Path.*, 134, pp. 99–106 (1989).
Everitt et al., Toxicol. Pathol. vol. 17, No. 3 (1989) pp. 465–473.
McLemore et al, Cancer Res 47 (Oct. 1, 1987) pp. 5132–5140.
Kitamura et al, Lab. Invest., vol. 62 No. 3 (1990) pp. 383–389.
Cobb, Exp. Lung Res., vol. 6 (1984) pp. 47–58.

*Primary Examiner*—Deborah Crouch
*Attorney, Agent, or Firm*—Harness, Dickey & Pierce, P.L.C.

[57] ABSTRACT

A non-human animal characterized by a human airway, the human airway being open-ended. The human airway is characterized by cells derived from the human respiratory system. The non-human animal and the human airway it carries are useful as models of human airways, particularly diseased human airways, for example, human CF airways. They are also useful to predict the efficacy or toxicity of agents and therapies on human airways, particularly on diseased human airways, for example, human CF airways.

8 Claims, 3 Drawing Sheets

NON-HUMAN ANIMAL MODEL OF A HUMAN AIRWAY

This invention was made with government support under Grant number R01 HL49040 awarded by the National Institute of Health. The government has certain rights in the invention.

This is a continuation of U.S. patent application serial No. 08/943,952, filed Sep. 11, 1992 now abandoned.

TECHNICAL FIELD OF THE INVENTION

This invention relates to a non-human animal characterized by a human airway, the airway having open ends, and to the open-ended airway itself. Preferably, the airway is a diseased human airway. More preferably, the airway is a human cystic fibrosis (CF) airway. Most preferably, the non-human animal in accordance with this invention is characterized by a xenograft of an airway populated by cells derived from the proximal or distal airways of a human lung, or mixtures of those cells, the ends of the airway being open to the air.

The non-human animal of this invention and the human airway it carries are useful as a model of a human airway and more preferably of a diseased human airway and most preferably of a human CF airway. They are especially useful as models to study the interrelationship and function of various cell types in human airways in general, and more preferably, in cystic fibrosis and other diseased airways and the genes and other molecules controlling such function. The invention is also useful as a model of human airways to assay the effect of various agents on human airways, and particularly the efficacy or toxicity of therapeutic and other agents, methods, and compositions, particularly those involved in gene transfer and manipulation, that may be used to treat lung disease, particularly cystic fibrosis, in humans.

BACKGROUND OF THE INVENTION

There are many diseases well known to affect human airways. Such diseases include, for example, cancer, cystic fibrosis, emphysema, asthma, tuberculosis and pneumonia. The study of these diseases and their treatment has, however, been hindered by the lack of a predictive animal model for a human airway, and particularly a diseased human airway and more particularly a human CF airway.

Cystic fibrosis (CF) is a lethal, inherited disease caused by abnormalities in epithelial cell function. The most morbid and life limiting aspect of cystic fibrosis involves pulmonary manifestations. The primary manifestation appears to be abnormal mucocilliary clearance. CF patients develop thick mucous that is difficult to clear and ultimately leads to obstruction of the airways. In addition, the lungs of CF patients become colonized with staphylococcus and pseudomonas and the patients suffer from recurring life-threatening pulmonary infections.

The gene responsible for CF is approximately 250 kbp and encodes a protein of 1480 amino acids. In approximately 70% of the individuals with CF, the CF gene is apparently dysfunctional due to a 3-bp deletion, which results in the deletion of a single amino acid (Phe-508). However, more than 170 different mutations have been identified in the remaining 30% of patients.

The CF gene product—the cystic fibrosis transmembrane conductance regulator (CFTR)—is thought to be a chloride channel normally expressed on the apical surface of epithelial cells. When the CF gene is dysfunctional, as in cystic fibrosis, the epithelial cells are incapable of properly transporting chloride and develop coordinate defects in sodium and water transport.

The primary pathogenic processes in CF involve the components of the lung that contribute to the mucous: the goblet cells which line the surface epithelium and the submucosal glands found in the proximal airway whose function is to produce mucous and transport it into the airway lumen. Expression of CFTR has recently been localized to both cell types. However, most animal models, including rodents and rabbits, lack submucosal glands in their airways, making them unsuitable for the study of cystic fibrosis and other lung diseases of humans.

The deficiencies of the currently available animal models for human cystic fibrosis lungs are best demonstrated by a study recently reported in Science [J. N. Snouwaerl et al., "An Animal Model for Cystic Fibrosis made By Gene Targeting"*Science*, 257, pp 1083–88 (1992)] in which investigators developed a mutant strain of mice deficient in the CF gene. While these animals developed many manifestations of cystic fibrosis, they lacked the lung pathology which characterizes the human CF disease.

Accordingly, in order to study the causes and pulmonary manifestations of cystic fibrosis and other human lung diseases, to study the effect of various agents, environmental and otherwise, on human airways and, particularly, to study the efficacy of various potential therapies or agents for human lung disorders, especially CF, a useful animal model of a human airway is urgently needed.

SUMMARY OF THE INVENTION

The present invention solves the problems referred to above by providing a non-human animal characterized by a human airway, the airway having open ends. More preferably, the human airway is a diseased human airway. Most preferably, the human airway is a human CF airway.

Typically, the non-human animal of this invention is characterized by a xenograft of an airway populated by cells derived from the airways of the human respiratory system. Preferably, the cells are derived from the airways of a patient having a lung disease. More preferably, the cells are derived from the airways of a CF patient.

The non-human animal and the human airways of this invention may be used as models of a human airway, preferably a diseased human airway, and more preferably of a CF human airway, to study the specific pathological processes that occur during human lung disease and particularly during the course of CF in humans. They are also useful to study the mechanism of action, efficacy and toxicity of drugs and other agents on the cells of normal or diseased human airways. The non-human animal of this invention and its human airway is also useful as a model to predict the efficacy or toxicity of such agents in humans, and particularly in human CF patients and patients with other lung disorders.

DETAILED DESCRIPTION OF THE INVENTION

Figure 1:
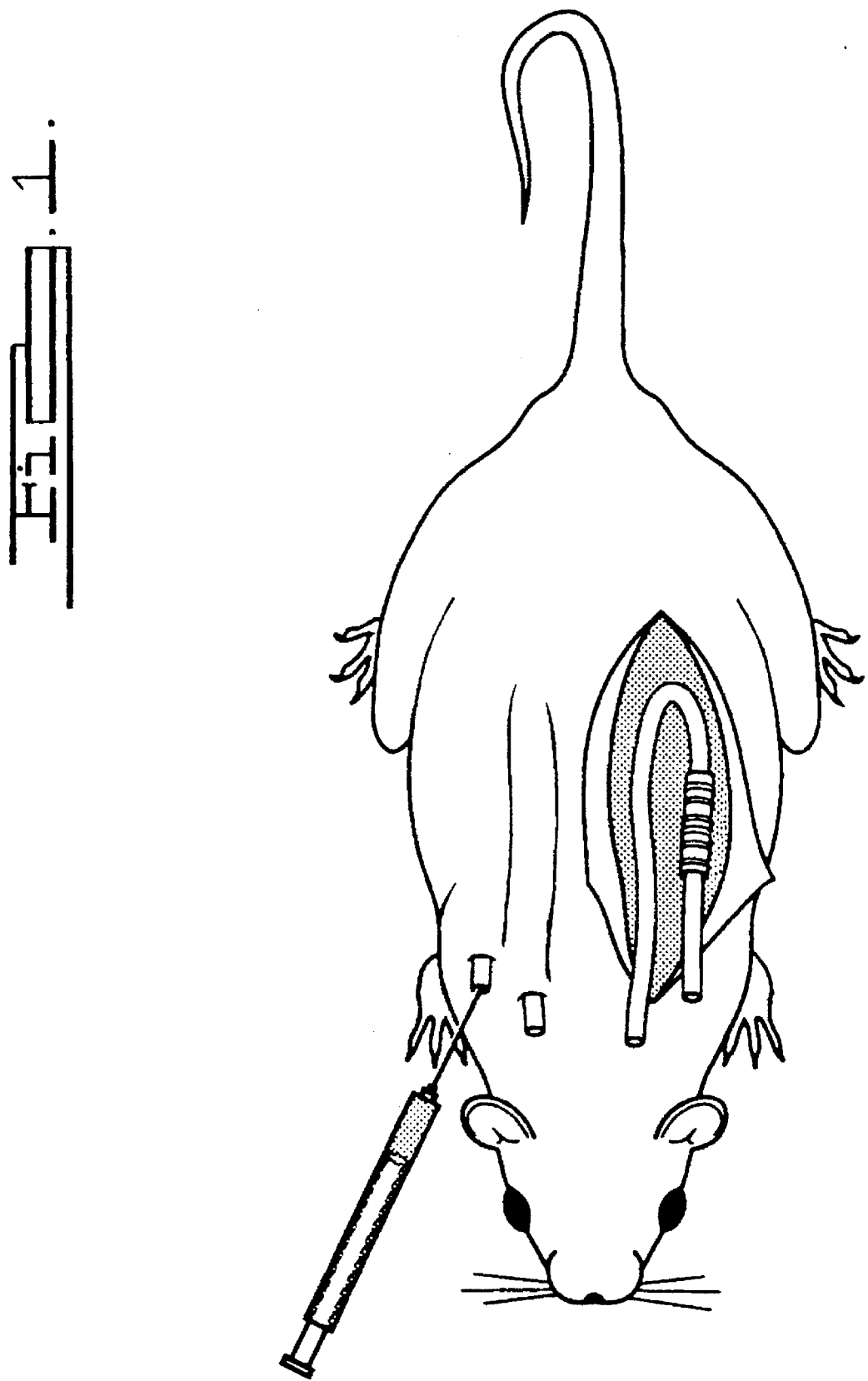
FIG. 1 depicts an open-ended xenograft, i.e., a xenograft ligated to flexible plastic tubing and implanted subcutaneously such that the ends of the tubing exit through the back of the neck.

This invention relates to a non-human animal characterized by a human airway, having open ends. Preferably, the airway is a diseased human airway. Most preferably, it is a human CF airway.

Because of the unique development of the cells in the open-ended human airways of this invention, those airways substantially reproduce the airway of the human patients from which the cells were derived. The open ends of the airways of this invention also permit the easy introduction of agents into those airways and the cells that characterize them and the easy clearance of those airways, particularly the CF airways, of mucous and other fluids. The airways of this invention are thus useful to study the relationship between particular agents and human lung disease, both positively and negatively. The airways also allow the observation and study of specific cellular functions and interactions that may be absent or altered in the lungs of animals, other than humans.

The diseased human airway of the preferred embodiment of this invention and the animal that carries it are useful as models for that disease and for assaying the effects of various therapies and agents on it. The human CF airway of the more preferred embodiment of this invention and the animal that carries it is particularly useful as a model of specific CF phenotypes resulting from specific CF genotypes, and is, thus, useful to study the response of specific CF genotypes to various potential therapies and other agents.

In order that this invention may be better understood, the following terms and definitions are herein provided.

"Non-human animal" is an animal, other than a human, that is capable of receiving a graft of a human airway as defined in this invention, without rejecting that graft. In a preferred embodiment, the non-human animal is a non-primate animal. In a more preferred embodiment, the non-human animal is a rodent. In the most preferred embodiment, the non-human animal is an athymic nu/nu mouse.

"Airway" includes any of the air-containing tubes of an animal, including human, respiratory system. It includes, without limitation, the trachea, the bronchi, and the bronchioles.

"Human airway" is an airway populated by cells derived from the airways of the human respiratory system, i.e., the proximal and distal airways of human lungs. The airway from which the cells are derived may be a normal human airway or a diseased human airway. Preferably, the cells are from a diseased human airway and most preferably they are from a human CF airway. Alternatively, they may be derived from a healthy human airway and subsequently altered in vitro, either transiently or genetically (e.g. by mutation or transfection or transformation with foreign DNA or other agents), to a disease, and preferably a CF, phenotype.

Preferably, the human airway of this invention is open-ended so that the cells will populate the airway and develop correctly in it in accordance with this invention. In addition, the open ends allow agents to be introduced into the airway and the airway to be flushed of mucous and other fluids and debris, ie., "coughed".

"Diseased human airway" is a human airway as defined in this invention, populated by cells of a human airway disease phenotype. Such diseases include, without limitation, cancerous and precancerous conditions, asthma, cystic fibrosis, emphysema, tuberculosis and pneumonia. Preferably, the cells are derived from an airway of a diseased human respiratory system.

"Human CF airway" is a diseased human airway as defined in this invention, populated by cells derived from a human CF phenotype. Preferably, the cells are derived from an airway of a human CF respiratory system.

"Open-ended graft" is a human airway having open ends. Preferably, this is achieved in accordance with this invention by ligating the airway to flexible plastic tubing and implanting the airway subcutaneously into a non-human animal, preferably onto its back, such that the ends of the tubing exit through the tissue of the animal and remain open to the air. See FIG. 1.

"Denuded airway" is an airway in which substantially all of the native epithelial cells have been removed. According to the preferred embodiment of this invention, the denuded airway is a rat trachea that has been denuded by several rounds of freeze-thawing. However, one of skill in the art will understand that airways from other animals, including humans, may also be useful in this invention. As will become apparent from the disclosure to follow, the primary consideration in the origin of the airway is the ease of excision, denuding, reseeding, implantation and manipulation after grafting.

The human airway and non-human animal characterized by the human airway of this invention are prepared using techniques and starting materials well known and available in the art.

The starting airway may be obtained from any animal, including a human. In the preferred embodiment of this invention, it is derived from a rat. The airway is isolated from the animal using conventional methods. For example, various well-known methods exist for isolating the most preferred rat trachea.

In the preferred embodiment of this invention, the airway, before being seeded with human cells, is denuded by conventional methods. More preferably, it is denuded using several rounds of freeze-thawing.

The denuded airway is then seeded with human cells derived from the airways of a human respiratory system, i.e., from the distal or proximal airways of a human lung. Those cells are isolated from the normal or diseased, particularly CF, human airway tissue using conventional methods, expanded in vitro with appropriate growth factors and antibiotics as is well known in the art and then resuspended and seeded into the denuded airways.

In order to produce an open-ended graft in accordance with this invention, each end of the airway is ligated to tubing, preferably flexible plastic tubing, such that when implanted into the non-human animal, the tubing will remain open to the surface. This ligation may occur before or after seeding of the cells.

The seeded, ligated airway is then grafted into a non-human animal using conventional methods, maintaining the ends of the graft outside of the animal and open to the air. The animal must be capable of receiving the graft without rejecting it. Preferably, the animal is immunodeficient, either genetically or transiently. Methods for producing such animals are well known.

The graft is then allowed to incubate in vivo. Preferable, incubation is for 1 to 6 weeks. During this time, the seeded cells develop and repopulate the denuded airway to form an airway substantially similar to the human airway from which the cells were derived. Thus, if the cells were derived from a normal human airway, the repopulated airway will be a model of a normal human airway. If the cells were derived from a diseased human airway, preferably a CF airway, the repopulated airway will be a model of the disease.

The airways and non-human animals of this invention are useful in a variety of ways. In one embodiment, this invention provides methods to study the delivery, mechanism of action, effectiveness or toxicity of therapeutic agents for human lung disease, particularly cystic fibrosis, and the lung conditions which may accompany those diseases. The method of this embodiment comprises the step of introducing the therapeutic agent into a human airway of this invention, preferably through the open ends of the airway, and assessing the effect of the agent on the function of the airway and the cells within it.

For example, a human airway according to this invention may be exposed to agents in liquid, gaseous, or solid forms that are suspected of affecting lung function or the course of human lung disease. For example, a human CF airway of this invention may be exposed to agents such as: amiloride and other agents which may affect the uptake of sodium ions by the respiratory epithelium; ATP, UTP and other agents which may result in chloride afflux, or DNAses and other agents which may affect viscosity or clearance of the mucus.

In addition, the efficacy or toxicity of gene therapy for human lung disease, particularly CF, may be assessed by exposing an airway of this invention to recombinant viruses, liposomes, DNA-protein complexes or other vehicles carrying foreign DNA. After uptake of the DNA by the cells of the airway of this invention, the airways and the cells within them can be studied in vivo or removed, to determine the amount, cell-specific location and effect of the gene therapy on the cells and the disease state.

In another embodiment of this invention, a diseased human airway of this invention may be exposed to agents that are known to complicate the course of a human lung disease. For example, the human CF airway of this invention may be exposed to Pneumococcus, Pseudomonas and other infective agents. The effect of these agents on the diseased airway may then be compared to their effect on a normal human airway of the invention in order to assess the differences in the physiological response to such agents.

In another embodiment of this invention, a normal human airway may be exposed to various agents, such as environmental agents, potential toxins, and cigarette smoke, in order to study the potential effect of those agents on human lungs. Such airways may also be used to assess the ability of various therapies and treatments to avoid or lessen the effects, if any, of such toxins and agents.

In another embodiment, this invention relates to methods of determining the mechanism of action, efficacy or toxicity of therapeutic agents which may be used to treat genetically based diseases such as cystic fibrosis. In this embodiment, the cells derived from an airway of the human respiratory system, are exposed to the agent or therapy before using the cells to seed the denuded airway. The effect of the agent or therapy on the ability of the cells to differentiate and repopulate the denuded airway, or the ability of the cells to function after repopulation of the denuded airway, is then assessed. This embodiment is useful to assess the potential effect of gene therapies and other treatments which may be administered in utero or before or during differentiation of lung tissue.

One particular advantage of this invention is the ability to tailor the CF airways to a particular genotype of interest. Because the CF airway will be substantially similar to the CF cells from which it was derived, specific mutations in the CF gene may be correlated with the phenotype of the disease produced, including the ability of that particular phenotype to respond to a given therapeutic agent or to interact with a given infective or complicating agent.

In order that this invention may be better understood, the following examples are set forth. These examples are for purposes of illustration only, and are not to be construed as limiting the scope of the invention in any manner.

EXAMPLES

I. Bronchial Epithelial Cell Isolation and Culture

We isolated approximately 5–20 gram samples of human bronchial epithelial tissue from large bronchial airways of either normal human lungs destined for transplantation or lungs from cystic fibrosis patients undergoing lung transplants at the University of North Carolina Medical Center, Division of Pulmonary Disease. We soaked and rinsed the tissue with Modified Eagles Medium (MEM) supplemented with 50 µg/mL penicillin, 50 µg/mL streptomycin, 40 µg/mL tobramycin, 50 µg/mL ceftazidime, 2.5 µg/mL amphoteracin B, 10 µg/mL DNAse, and 0.5 mg/mL dithiothreotol for 4–12 hours at 4° C. The tissue was then transferred to MEM medium supplemented with 0.1% protease-14 and incubated for 30–34 hours at 4° C. We then added fetal calf serum (FCS) to a final concentration of 10% and removed the cells into the medium by agitation and blunt scraping. The removed cells were then pelleted, washed twice in Hams F12 containing 10% FCS and cultivated on uncoated plastic tissue culture plates at a density of $2 \times 10^6$ cells/100 mm plate. The cultivation medium was hormonally defined Hams F12 medium containing 1 µM hydrocortisone, 10 µg/mL insulin, 30 nM thyroxine, 5 µg/mL transferrin, 25 ng/mL epidermal growth factor, 3.75 µg/mL endothelial cell growth supplement, 10 ng/mL cholera toxin, 50 µ/mL penicillin, 50 µg/mL streptomycin, 40 µg/mL tobramycin, 50 µg/mL ceftazidime, and 2.5 µg/mL amphoteracin B. We replaced the medium with fresh medium at 36 hours and every 24 hours after that. On the fourth day, we harvested the cells by treatment with 0.1% trypsin followed by addition of 10% FCS/Hams F12. We then pelleted the cells and resuspended them at a concentration of $2 \times 10^4$ or $2 \times 10^6$ cells per 30 µl hormonally defined media for seeding into denuded rat trachea.

II. Establishment of Xenografts

We harvested rat trachea from $CO_2$ asphyxiated male Fisher 344 rats (200–250 g) and denuded the trachea by three rounds of freeze/thawing followed by rinsing of the lumen with MEM. We then seeded the denuded rat trachea as follows.

We injected the bronchial epithelial cells into the lumen of the denuded trachea. We then ligated both tracheal ends to flexible plastic tubing by tying silk suture thread circumferentially around the tubing. we then implanted these xenografts subcutaneously into the flanks of nu/nu balb C mice anesthetized by intraperitoneal injection of 100 mg/kg ketamine and 20 mg/kg xylazine. We sutured the implanted tracheas such that the ends were kept open to the surface via the plastic tubing, which was tied to the proximal and distal ports of the graft, tunnelled subcutaneously, and exited percutaneously through the back of the neck. This suturing technique, which produces open-ended xenografts, is shown in FIG. 1. Open-ended xenografts allow easy accessibility to the lumen of the graft, eg for introduction of various liquid, gaseous or solid agents or for removal of mucous, fluid and other biological components of the graft. We irrigated the xenografts weekly with Hams F12 medium to prevent accumulation of mucus.

An alternative method of graft implantation is to ligate the trachea closed at both ends before implantation. However, we found that if the tracheas were not irrigated regularly, they accumulated increasing quantities of mucus that eventually led to distortion of the graft. The implantation of closed xenografts also prevented full differentiation of the epithelial tissue within the airway. After 3 to 6 weeks incubation, the reconstituted epithelium contained major areas of a squamous or cuboidal epithelium, as well as pseudostratified morphology.

III. Analysis of the Xenografts

When we produced open-ended xenografts from normal bronchial tissue, the resulting fully mature graft produced a pseudostratified epithelium along the entire surface of the trachea that was indistinguishable from that of a normal bronchus. We analyzed the grafts by electron microscopy as follows.

We excised the xenografts and rinsed them briefly in phosphate buffered saline (PBS) and then fixed overnight in 2.5% glutaraldehyde, 1.5% paraformaldehyde, 0.02% $CaCl_2$ in 0.1M sodium cacodylate (pH 7.4) at 4° C. Following fixation, we washed the tissue repeatedly in 0.1M sodium cacodylate, postfixed in 1% osmium tetroxide for 1 hour at 0° C., dehydrated in alcohols, and embedded the tissue in epoxy resins. We then stained sections with uranyl acetate and lead citrate before viewing and photographing with a Hitachi 11a electron microscope.

Figure 2:
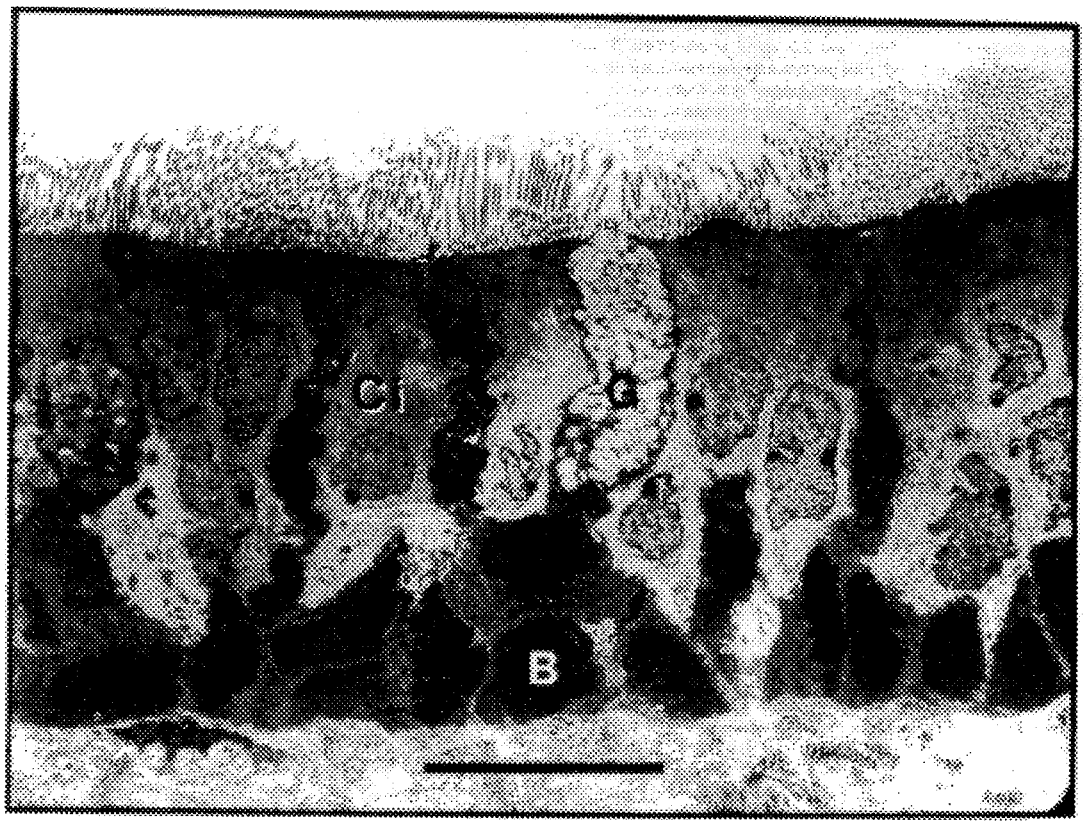
FIG. 2 depicts an election micrograph of a xenograft from a normal human lung.

An electron micrograph of a typical xenograft from a normal lung is shown in FIG. 2. All cell types were represented including a layer of basal cells, ciliated cells, secretory goblet cells, and nonciliated columnar cells.

IV. Analysis of Morphology and Proliferative Activity of Open-Ended Xenografts

Light microscopic analysis of grafts seeded at low density ($2 \times 10^4$ cells) revealed relatively undifferentiated morphology. Cells were either squamous or cuboidal in shape and were frequently stratified into multiple layers. None of the cells appeared to polarize, contain cilia, or react to alcian blue/PAS. When grafts seeded at low density were incubated with BrdU in order to assess the overall state of cell proliferation at the time of retroviral infection, $40 \pm 4\%$ of the cells were mitotically active (data not shown). These studies indicate that after one week, grafts seeded with $2 \times 10_4$ cells contain an undifferentiated epithelium that is rapidly regenerating. If left in the mice for 6 weeks, these grafts become quiescent and fully differentiated.

Grafts seeded at high density ($2 \times 10^6$ cells) develop a fully differentiated epithelium within 3 weeks. We compared the localization of CFTR in the fully differentiated graft to that in normal human bronchus, by staining with a polyclonal antibody made to the COOH terminus of CFTR. Briefly, we sectioned fresh frozen xenograft tissue at 6 μm onto poly (1-Lysine) -coated slides and fixed in acetone for 10 minutes at −20° C. followed by air drying. We then blocked the sections in 20% DS in PBS for 30 minutes and added an affinity purified rabbit polyclonal antibody (α–1468) which recognizes residues 1468–1480 of CFTR [J. A. Cohn et al., "FTR: Development of High-affinity Antibodies and Localization In Sweat Gland", Biochem. Biophys Res. Commun., 181, pp. 36–43 (1991)].

Figure 3:
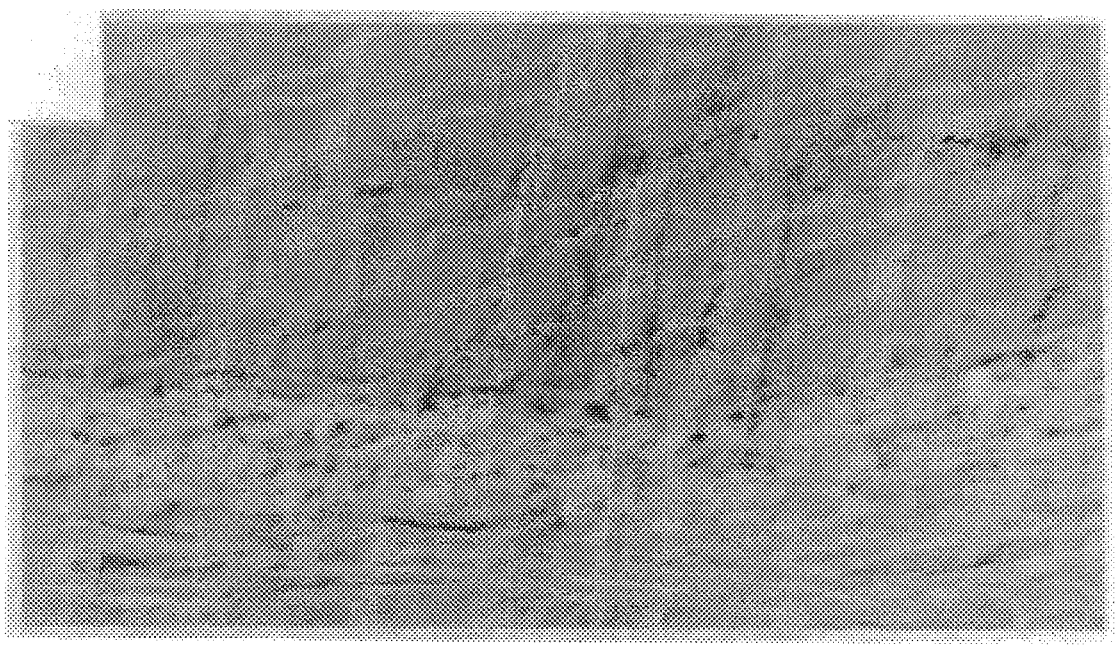
FIG. 3 depicts the CFTR staining pattern with a fully differentiated xenograft from a normal human lung.

As shown in FIG. 3, the staining pattern within a fully differentiated graft is virtually identical to that seen in normal human bronchial samples. Low level staining is detected on the apical surface of columnar epithelial cells while a higher level of staining is seen in basal and intermediate cells. In summary, after three weeks, open-ended xenografts produced from normal human bronchial epithelial cells seeded at high density produce an epithelium that closely resembles that of a normal, unperturbed, human main stem bronchus.

When we analyzed the fully developed open-ended xenografts produced from the CF epithelial cells, i.e., CF airways, we found a statistically significant decrease in the abundance of goblet cells compared to the CF bronchial tissue from which the xenograft was derived. Table I compares the distribution of the three most abundant cell types in the bronchial airway: basal cells, ciliated cells, and goblet cells.

TABLE I

|  | Basal Cells | Ciliated Cells | Goblet Cells |
| --- | --- | --- | --- |
| CF xenograft | 38.0% | 37.7% | 24.3% |
| CF bronchial tissue | 33.4% | 34.7% | 32.0% |

This suggests that goblet cell hyperplasia within the airways of CF patients is most likely a secondary complication of bacterial infection and not a primary defect in the regulation of goblet cell development and proliferation. Because the CF airway in a non-human animal is the same genetically as the CF lung from which it was derived, these data demonstrate how the CF airway may be used to study the environmental elements involved in the disease course of CF. For example, bacteria, mucous and other agents can be introduced into the CF airway and assessed for their ability to shift the properties and relative populations of the various cell types, as well as the function of the airway as a whole.

We claim:

1. A non-human animal model of a human airway, wherein the non-human animal is an immunocompromised rodent and the airway has continuously open ends and supports a fully differentiated epithelium around its lumen.

2. The non-human animal model of claim 1, wherein the airway is selected from an animal, including human, trachea, bronchi or bronchioli repopulated with cells from a human airway.

3. The non-human animal model of claim 1 or 2, wherein the human airway is a diseased human airway.

4. The non-human animal model of claim 3, wherein the human airway is a human CF airway.

5. The non-human animal model of claim 1, wherein the animal is a nu/nu mouse.

6. A method for producing a human airway which has continuously open ends and supports a fully differentiated epithelium around its lumen comprising the steps of:

(1) denuding an isolated airway of an animal, including human, respiratory system;

(2) seeding the denuded airway with cells from an airway of a human respiratory system;

(3) ligating tubes onto denuded airway before or after seeding it with the cells;

(4) grafting the resulting seeded airway into an immunocompromised rodent while maintaining the ends of the tubes outside of the rodent and open to the air; and (5) incubating the grafted airway to allow the cells to repopulate the airway while maintaining the ends of the tubes outside of the rodent and open to the air.

7. The method of claim 6, wherein the human airway is a diseased human airway.

8. The method of claim 6, wherein the human airway is a human CF airway.

* * * * *